(12) United States Patent
Ollivier

(10) Patent No.: US 9,339,646 B2
(45) Date of Patent: May 17, 2016

(54) SYSTEM FOR STIMULATION AND/OR DEFIBRILLATION OF THE LEFT VENTRICLE ENDOCARDIALLY OR FROM A VEIN IN THE CORONARY SYSTEM

(75) Inventor: Jean-Francois Ollivier, Villiers-le-bacle (FR)

(73) Assignee: SORIN CRM SAS, Clamart (FR)

( * ) Notice: Subject to any disclaimer, the term of this patent is extended or adjusted under 35 U.S.C. 154(b) by 1050 days.

(21) Appl. No.: 13/306,934

(22) Filed: Nov. 29, 2011

(65) Prior Publication Data

US 2012/0136423 A1 May 31, 2012

(30) Foreign Application Priority Data

Nov. 29, 2010 (FR) ..................................... 10 59847

(51) Int. Cl.
*A61N 1/05* (2006.01)

(52) U.S. Cl.
CPC .............. *A61N 1/056* (2013.01); *A61N 1/0563* (2013.01); *A61N 1/057* (2013.01); *A61N 2001/0585* (2013.01)

(58) Field of Classification Search
CPC ..... A61N 1/056; A61N 1/0563; A61N 1/057; A61N 2001/0585
USPC ................................................. 607/122, 126
See application file for complete search history.

(56) References Cited

U.S. PATENT DOCUMENTS

| 8,417,332 | B2 | 4/2013 | Ollivier |
|---|---|---|---|
| 2001/0012958 | A1 | 8/2001 | Audoglio |
| 2003/0023296 | A1 | 1/2003 | Osypka |
| 2006/0064150 | A1 | 3/2006 | Heist et al. |
| 2009/0221895 | A1 | 9/2009 | Osypka |
| 2010/0069983 | A1 | 3/2010 | Peacock, III |
| 2012/0130464 | A1 | 5/2012 | Ollivier |

FOREIGN PATENT DOCUMENTS

| EP | 0 993 840 | 4/2000 |
|---|---|---|
| EP | 1 557 194 | 7/2005 |

OTHER PUBLICATIONS

Preliminary Search Report for French Patent Application No. 1059847, dated May 19, 2011, 2 pages.

*Primary Examiner* — Tammie K Heller
(74) *Attorney, Agent, or Firm* — Foley & Lardner LLP

(57) ABSTRACT

A system for stimulation/defibrillation of the left ventricle endocardially or from a vein in the coronary system including: a lead body (10) having a lumen, a distal end (12) with an anchor (14) connectable to a wall of a heart chamber or of a vein of the coronary system, and a proximal side with a connector (22) having a first terminal (26). The lumen of the lead houses a microcable (28) with an active free part (30) that emerges from the distal end. An insert (38) formed on the lead body includes a first electrical connection to the first terminal (26) of the connector, and a coupler selectively movable between (i) a released position wherein the microcable is free to slide in lumen of the lead body, and (ii) a closed position, wherein the microcable is both mechanically immobilized in the lead body and electrically connected to first electrical connection.

9 Claims, 4 Drawing Sheets

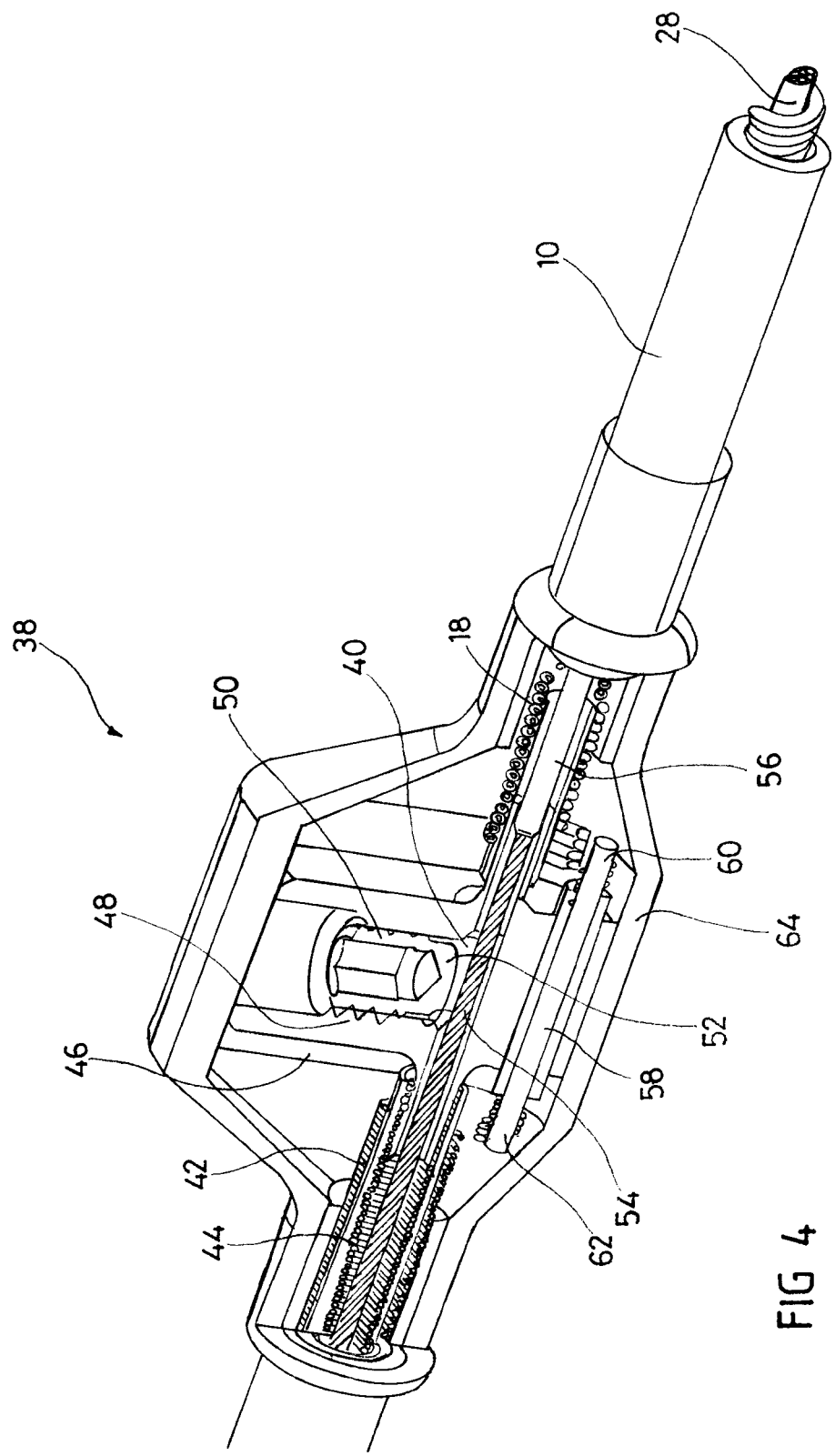

SYSTEM FOR STIMULATION AND/OR DEFIBRILLATION OF THE LEFT VENTRICLE ENDOCARDIALLY OR FROM A VEIN IN THE CORONARY SYSTEM

RELATED APPLICATIONS

The present application claims the benefit of French Application No. 10/59847 entitled "System For Endocardial Stimulation/Defibrillation Or For Stimulation/Defibrillation From A Vein In The Coronary System Of The Left Ventricle" and filed Nov. 29, 2010, which is hereby incorporated by reference in its entirety.

FIELD OF THE INVENTION

The present invention relates to "active implantable medical devices" as defined by the 20 Jun. 1990 Directive 90/385/EEC of the Council of the European Communities, more particularly to devices that continuously monitor a patient's heart rhythm and deliver to the heart, if necessary, electrical stimulation, resynchronization, cardioversion and/or defibrillation pulses, and even more particularly to a lead for the stimulation of the left ventricle on an endocardial site by direct application of pulses on the inner ventricular wall, or indirectly from a vein in the coronary network.

BACKGROUND

"Pacing" leads as used in this description refers to leads for the delivery of low-energy pulses used for bradycardia or resynchronization therapies. It should be understood, however, that the invention also applies to cardioversion/defibrillation leads for delivering high energy electric shocks to the heart for terminating a tachyarrhythmia. Unless otherwise stated, the terms "stimulation lead (or electrode)" or "pacing/defibrillation lead (or electrode)" should be understood generally to mean and include any type of lead used for these purposes.

For endocardial stimulation of a left heart cavity, with the known techniques, it is necessary to achieve a puncture in the septal wall having a sufficient diameter to introduce a guide catheter. The guide catheter is used to establish communication between the right ventricle and the left ventricle through the wall of the septum in order to introduce into the latter a left endocardial pacing lead.

French application No. 10/53499 filed May 5, 2010 entitled "Endocardial Stimulation/Defibrillation System of the Left Ventricle" and its counterpart U.S. patent application Ser. No. 13/101,508, commonly assigned herewith to Sorin CRM S.A.S. of Clamart France, propose to remove the guide catheter associated with a lead through the septum, replacing this system by a conventional lead screwed onto the wall of the right ventricle in the septum, and extending the lead using a partially isolated transeptal microcable, that is pushed into the left ventricle until it comes into contact against a target site located in the left ventricle, for example, against the free wall of the latter.

In this case, the lead is used not only as a support for at least one sensing/pacing electrode, but also as a tool for guiding the microcable through the wall of the septum (to make a puncture allowing the microcable to pass through the wall) and beyond, into the left cavity.

The puncture can be performed by a simple mechanical push of the microcable if the rigidity of the microcable latter is sufficient. But the drilling in the interventricular septum is preferably assisted by a RF puncture technique, which involves applying a localized radio frequency energy (RF) produced by a suitable electronic generator to create a very small size opening in the tissue of the septal wall. The puncture is obtained by combining, on the one hand, the function obtained by the screw lead guiding the microcable with, on the other hand, the application of RF energy sufficient to allow the microcable to gradually penetrate through the septum and thus greatly minimize the axial force required to be transmitted at the proximal end of the microcable during this step. Indeed, in the absence of an applied RF energy, a microcable that is too thin could not penetrate the tissue and would buttress at the point of contact with the wall of the septum. Note also that the RF puncture technique advantageously provides a cauterizing of the traversed tissues, and thus prevents significant bleeding.

After drilling through the septum walls, the microcable is pushed beyond the septum, now crossed from one side to the other side, with a free part, the length of which can be up to about 120 mm, emerging in the interior volume of the left ventricle, beyond the intermediate portion enclosed in the septum. This emerging free part of the microcable is totally or partially bared and is an active portion coming into contact in one or more points with the wall of the left ventricle.

Once the system is thus implanted, the pulse generator is connected to the lead and to the microcable, with one terminal of the detection/stimulation circuit connected to the distal electrode of the lead (e.g., an electrode located in the right ventricle), and the other terminal of the same circuit connected to the free part of the active microcable (e.g., the free part localized in the left ventricle).

The application between these two electrodes of stimulation pulses produce an electric field encompassing a large part of the cardiac mass, thus allowing an effective stimulation of the left ventricle.

In one embodiment, the active part of the microcable emerging in the left ventricle has a much smaller length (about 10 mm or less) with a loop, so as to press the end of the microcable against the wall of the septum on the left ventricular (LV) side, thus defining a located stimulation site. The stimulation remains endocardial, but the mobility of the microcable and the surface thereof exposed to the arterial circulation are greatly reduced.

This lead configuration can also be applied to the case of a defibrillator. The free part of the active microcable is then connected to one terminal of the shock circuit of the generator, the other terminal of which is connected to: a right ventricular (RV) coil placed in the right ventricle, and/or a superior vena cava (SVC) coil placed in the superior vena cava near the right atrium, and/or to the housing of the generator, and/or the distal electrode of the lead if it has a sufficient area. Such a configuration advantageously allows covering a maximum heart mass, despite the relatively small electrode surface compared to a conventional shock electrode. In addition, the shock is applied between electrodes located on either side of the septum, the latter being "squeezed" in the electric field. This allows to further increase the effectiveness of defibrillation at constant energy, or to significantly reduce the energy of the delivered shock and therefore the associated pain, compared to a conventional configuration wherein the shock would be delivered between the housing of the generator and the RV and/or SVC coils.

Another application of the microcable described above is described in French application No. 10/59521 filed Nov. 19, 2010, for a "stimulation lead of a left cavity of the heart, implanted in the coronary system," and corresponding U.S. patent Ser. No. 13/300,451 filed Nov. 19, 2011 (commonly assigned herewith to Sorin CRM S.A.S., of Clamart, France)

which proposes to stimulate the left ventricle, to introduce the lead and the microcable in the coronary system rather than the cavity to be stimulated, the lead being extended by the free active part of the microcable with its stimulation electrodes applied against the wall of the epicardium at the level of the left heart cavity to be stimulated. The microcable overcomes the difficulties associated with the gradual reduction in diameter of the veins as the lead progresses in the selected coronary vein, and to multiple the points of contact with the epicardium, thus maximizing the effectiveness of the stimulation. This overcomes the difficulties encountered with conventional leads to find a satisfactory stimulation site, get a good electrical contact of the electrode against the tissue of the epicardium, and maintain this contact, despite the various changes or stresses over time.

The present invention relates to a specific stimulation system configuration (lead plus microcable) that is particularly well suited for the implementation of the techniques described in the aforementioned French patent application FR 10 53499 and its counterpart U.S. patent application Ser. No. 13/101,508, and FR 10 59521 and its counterpart U.S. patent application Ser. No. 13/300,451, the disclosures of which are incorporated herein by reference in their entirety.

It is desirable to provide a stimulation system configuration that:

Establishes a simple and reliable electrical connection between, on one hand, the distal or proximal electrode at the distal end of the lead and the microcable, and, on the other hand, the terminals for a standard connector (for example, an IS-1, IS-4 or DF-4 type connector) at the proximal end of the lead;

Adjusts accurately the length of microcable emerging in the left ventricle, for example, in a range of lengths from 5 mm (e.g., contact with the septum, left ventricle side) to 120 mm (e.g., contact with the left ventricle free wall), or in the coronary system;

Guarantees a guiding push on the microcable to puncture the wall of the septum during progression in the coronary system, avoiding any risk of kinking of the microcable when it is not wrapped by the lead;

Requires only simple and fast gestures already known by the surgeons, and not requiring specific training or any use of special tools;

Permits repositioning of the microcable during implantation of the stimulation system (possibly multiple times) and/or after surgery.

The known devices proposed in the following publications have not met these requirements.

US Patent Publication No. 2001/0012958 A1 and 2010/0069983 A1 implement a classic probe (probe body forming the content) sliding in another conventional probe (probe body forming a container or guide) with a proximal side port through which emerges the probe body forming content.

US Patent Publication No. 2006/0064150 A1, for its part, offers a solution with two separate single-pole electrical outlets, with a single connector variation obtained by adding a parallel branch-type bypass.

US Patent Publication No. 2003/0023296 A1 has no telescopic function, even if it is otherwise an essential component of the system considered above.

None of these prior known publications disclose establishing an electrical connection between, on one hand, all distal electrodes and, on the other hand, a single proximal IS1 or IS4/DF4 type connector while avoiding the disadvantages of standard multi-line connection and providing a major advantage of simplicity of implementation on the operative field (e.g., no connection error to the head of the case, and a reduction of the volume of the system). In addition, these prior known publications either do not or hardly address the two critical issues of leakage and continuity of the electrical line, which are by nature a source of complication of a telescopic lead system. Moreover, the known solutions consisting of "stacking" conventional leads having to slide to (i.e. with a functional space between them) lead to larger sizes, which is inconsistent with the applications described above.

OBJECT AND SUMMARY

To this end, the present invention provides a system for the stimulation/defibrillation of the left ventricle either by an endocardial approach (i.e., "endocardially") or from a vein in the coronary system, including: a lead body made of deformable material and having an internal lumen with a proximal end and a distal end, the distal end having means for anchoring the distal end of the lead body to a wall of a heart chamber or to a vein of the coronary system, and the proximal side having a connector with a first terminal, and at least one electrically conductive microcable that is housed in and sliding along the lumen of the lead body extending the entire length of the lead body and beyond the distal end thereof, the microcable having a distal end with a free active part comprising at least one bared conductive region, and an insert formed on the lead body in a proximal region thereof. The insert includes a first electrical connection to a first terminal of the connector, and a coupling mechanism or coupler that is selectively moveable between (i) a released position, wherein the microcable is free to slide in the lumen of the lead body, and (ii) a closed position, wherein the microcable is both mechanically immobilized in the lead body and electrically connected to said first electrical connection.

In one embodiment, which is particularly suitable for endocardial stimulation, the lead body includes at least one insulated conductor extending along the entire length of the lead body and at least one electrode for stimulation and/or defibrillation. The connector preferably includes a second terminal connected to the stimulation/defibrillation electrode via said insulated conductor extending along the lead body. The insert is electrically insulated and has a proximal side and a distal side and includes: a first interval of interruption of the insulated conductor; on the proximal side of the interval, a second electrical connection to said second terminal of the connector; on the distal side of the interval, a third electrical connection to the insulated conductor; and a connection, in circumvention of the first interval of interruption, from the second electrical connection to the third electrical connection.

In a preferred embodiment, the coupler includes a screw radially oriented relatively to the direction of the lead body, with an inner end for penetrating in the interval to come in radial support against the microcable, and an outer end including an apparent receptacle or receptacle or footprint for receiving a screwing tool.

In one embodiment, the system further includes a stylet for pushing the microcable in the lead body, and the microcable is terminated at its proximal end by a receptacle for receiving the distal end of the pushing stylet. One such receptacle is a hollow spring cone-shaped receptacle for being screwed with the distal end of the pushing stylet. In an alternative embodiment, the stylet is terminated at its distal end by a socket created by local deformation of a hypotube, and can be inserted directly with a controlled force on the microcable. The term "hypotube" as used herein refers to a tube of small dimensions, of which one such non-limiting example is a tube having an outer diameter of about 0.5 mm, an inner diameter of about 0.35 mm, and a length of about 5 mm, with the dimensions being variable according to the design preference of any specific application.

In a preferred embodiment, the lead body and microcable are dimensioned so that when at the distal end of the microcable flushes the outlet of the lumen of the lead body, the proximal microcable is then fully inserted into the assembly formed by the body lead and the connector.

In one embodiment of the invention, the microcable includes near its proximal end, in the region between the proximal end and the insert, a stop ring attached to the microcable. The diameter of the stop ring is greater than the diameter of the bore of the insert receiving the microcable at the proximal side, to limit the sliding of the microcable in the lead body, and consequently the length of the part emerging beyond the distal end of the lead body, to a predetermined maximum length;

In yet another embodiment, the lead is made of two separable parts, with (i) one part forming the lead itself, terminated at its proximal end by a first plug, and (ii) the other part forming an extension portion terminated at its distal end by a second plug, the second plug being a counterpart of the first and a proximal side said connector, and wherein the insert is formed on the extension portion.

DRAWINGS

Further features, characteristics, and advantages of the present invention will become apparent to a person of ordinary skill in the art from the following detailed description of preferred embodiments made with reference to the annexed drawings, in which:

FIG. 4 is an enlarged view of the insert of FIG. 3.

DETAILED DESCRIPTION

With reference to the drawings, FIGS. 1-4, preferred embodiments of a system for stimulation/defibrillation of the left ventricle, in accordance with the present invention, will now be described.

Figure 1:
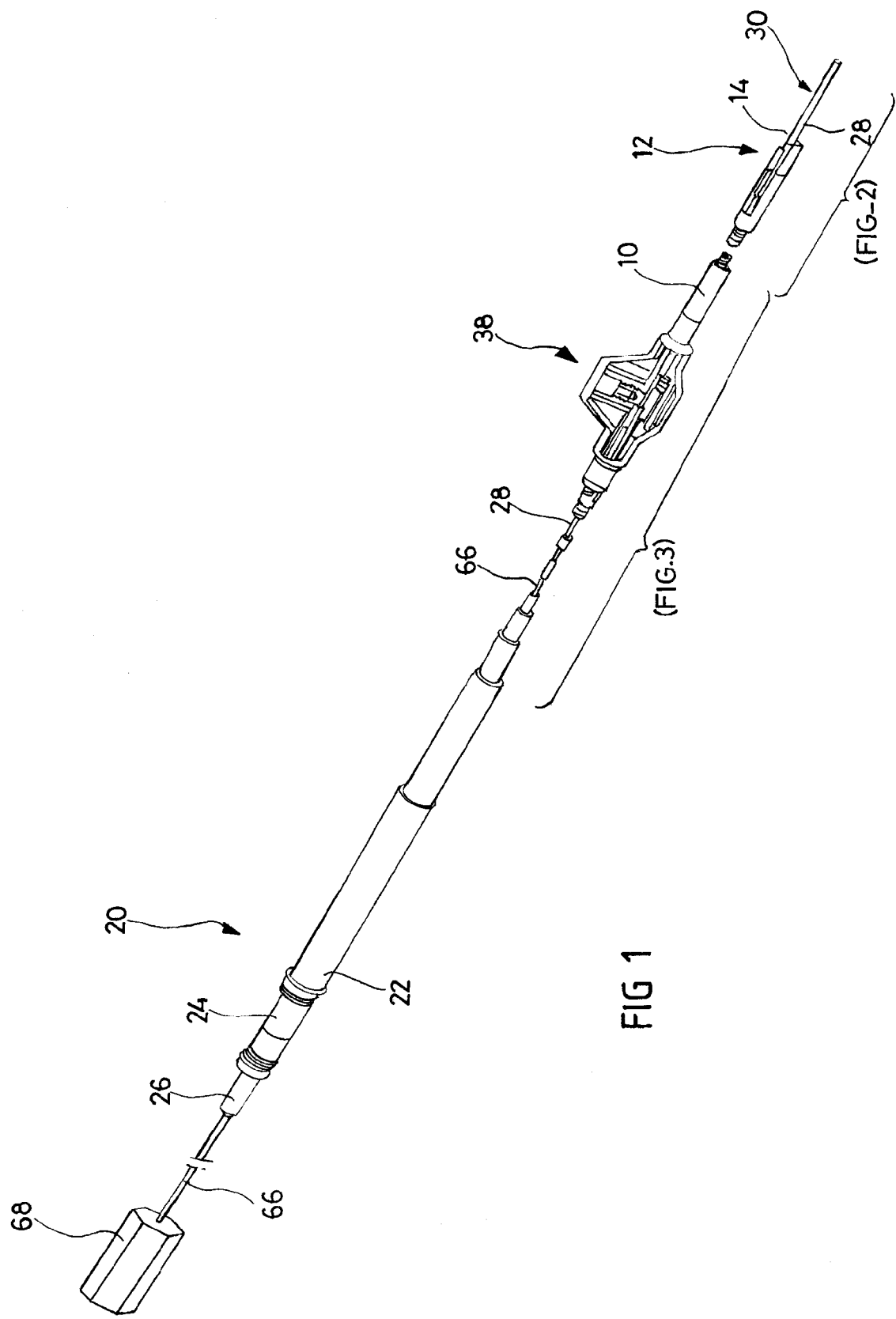
FIG. 1 is an elevated perspective, partial cross-sectional view of a preferred embodiment of a system of the present invention.
Figure 2:
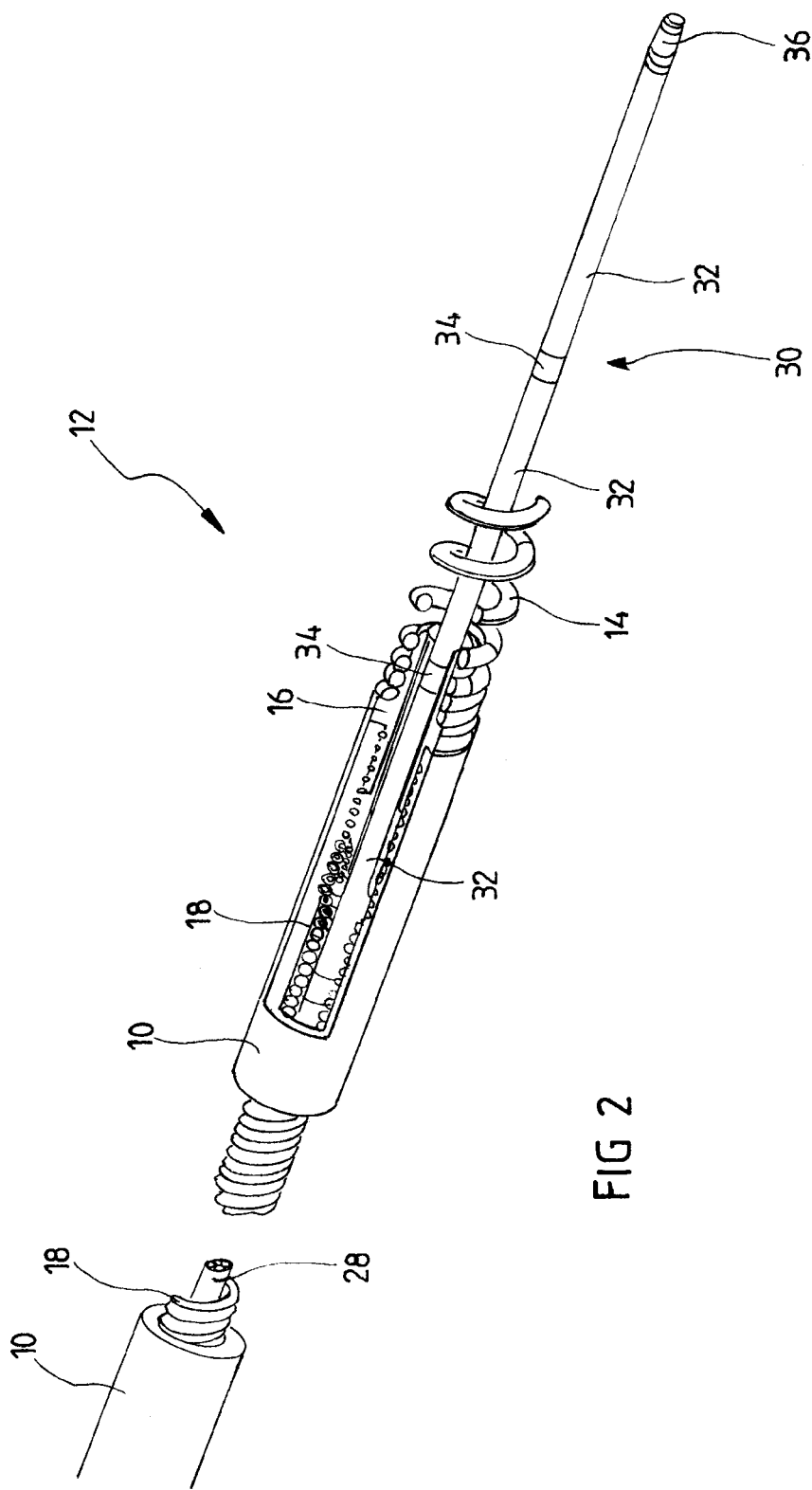
FIG. 2 shows an enlarged and partially cross sectional view of the distal end region labeled FIG. 2 of the system of FIG. 1.

A system in accordance with a preferred embodiment includes a first lead with a distal part having a conventional structure, corresponding, for example, to the structure of models Stelid BS46D or BeFlex RF46D marketed by Sorin CRM, Clamart, France (these models, however, do not have insulated conductors). This lead includes a lead body 10 having a conventional structure, with an outer sleeve made of a deformable material, typically a polyurethane or silicone. The lead body is terminated at its distal end 12 with a lead head including a helical screw 14 made of non-touching turns with a diameter of, e.g., about 1 to 2 mm (shown in more detail FIG. 2). This screw is fixed to the lead head by a tip 16 having at its center a lumen and a sealing means, the latter being, for example, a pierced silicone plug to prevent any backflow of blood inside the lead body both in the absence and in the presence of an element introduced into the central lumen and penetrating the pierced silicon plug (as illustrated in FIG. 2).

The tip 16 is preferably made of metal and also acts as a distal electrode. This electrode (or alternately or in addition a specific annular electrode carried by the lead) is electrically connected to an insulated inner conductor 18, such as a coiled conductor extending along the whole the length of the sheath to the proximal end 20, opposite, of the lead. For example, a suitable conductor is that of the same type used in the commercial lead model Xfine TX26D marketed by Sorin CRM, Clamart, France. End 20 is terminated by an electrical connector 22 intended to be coupled to the housing of an implanted generator such a pacemaker/defibrillator or resynchronizer.

The material and dimensions of the sheath lead body 10 can be chosen, in combination with the dimensions of spiral conductor 18, to provide some torsional rigidity of the lead body, so as to transmit a torque from the proximal end 20 of the present lead (at the electrical connector 22) to the distal end 12 of the lead. This rotation move should allow the screw 14 to rotate for screwing it to penetrate into the heart tissue.

The connector 22 includes two electrodes (at least), with an annular or "ring" electrode 24 designed to be connected to the electrode 16 carried by the lead, and an end or "tip" electrode 26 for being connected to the microcable to be introduced into the lead body. The method in accordance with a preferred embodiment of the present invention, by which the two respective electrical connections are established, is described below.

As shown in the drawings, a microcable 28 is introduced into the central lumen of the lead body 10 to the tip 16 and through the pierced silicone plug at tip 16 in order to emerge beyond the distal end of the lead body on a free part 30, the emergence of which can be controlled. Initially, microcable 28 typically abuts against the wall of the septum, and is substantially oriented in the direction of the central axis of the screw 14.

The preferred diameter for the core of microcable 28, that is to say, of the non-insulated metal part, is between about 0.1 and 0.3 mm. The isolation of this core is provided by an insulating sheath made of parylene, polyurethane, silicone, or ETFE, or a comparable material, leading to a total outer diameter of about 0.3 to 0.5 mm for the microcable with its sheath.

These dimensions are smaller when compared to the diameter of about 0.8 mm of the puncture needles of the standard transeptal kits (drilling in the atrial septum with femoral access), of 7 French (2.33 mm) or 9 French (3 mm) catheters, and of 5 French (1.66 mm) or 6 French (2 mm) leads used in the conventional techniques of implantation of a left endocardial lead, with a transeptal approach. The microcable of the present invention, even coated with an insulating sheath, is thus of a much smaller diameter than what is usually used for transeptal procedures.

Microcable 28 is advantageously made based on nitinol (NiTi alloy), a material whose main advantage is its extreme fatigue endurance (durability). Specifically, the structure of the microcable is a multi-wire structure in which each strand consists of a core of platinum-iridium (for radiopacity) coated by nitinol (or vice versa). Optionally, the assembly is then covered either by a thin layer of parylene (e.g. of C-type) or by a polyurethane tube.

These types of microcables are available, for example, from Fort Wayne Metals Company Inc., Fort Wayne, USA, and are used in the medical field including the manufacturing of defibrillation conductors—but in a different arrangement of material. In the prior known applications, the structure is a multi-wire structure in which each strand includes a core of silver (to improve conductivity) coated with a stainless steel. These microstructures, isolated or not, are then incorporated into a multi-lumen lead body of a classic known construction.

The benefits of the microcable structure in accordance with the present invention as described above lies in the fact that the less mechanically durable elements (platinum-iridium or silver) are directly encapsulated in the nitinol sheath. The consequences of a possible fracture of these strands are thus minimized.

Alternatively, it is nevertheless possible to have a strand of platinum-iridium in the center of a 1×7-type multi-wire structure, the most fragile strand being then embraced by the more durable external strands.

Finally, platinum-iridium can be replaced by any radio-opaque material such as tantalum, and nitinol can be replaced with sufficiently functional but less durable or less expensive materials, such as MP35N stainless steel, commonly used in the manufacture of the standard conductors.

The active part 30 of microcable 28 (i.e., the part emerging from end 12) has a plurality of bared parts forming a succession of individual electrodes electrically connected together. For example, in the example (not limitative) shown in the figures, the insulating coating 32 is interrupted so as to define a succession of bare short annular zones 34, the microcable being terminated by a distal electrode 36.

This configuration can be performed by successively and alternately threading insulating tubes (to form the regions 32) and conductive rings, for example, crimped on the microcable (to form the bared areas 34). Alternatively, and especially if the core of the microcable is coated with a thin insulating parylene layer, the configuration is performed by arranging openings in the insulation along the microcable, for example, by plasma ablation, to form the bared areas 34 and 36. To improve the electrical performances, these areas may further be coated with a conductive material, for example, titanium nitride.

The configuration just described corresponds essentially to that described in patent application FR 10 53499 and its counterpart U.S. patent Ser. No. 13/101,508, identified above.

The characteristic features of the present invention will now be described.

The present invention provides the surgeon a simple and reliable system and method to establish an electrical connection between microcable 28 and the corresponding terminal of the connector 22 after exactly setting the emerging length of the free active part of microcable 28 to the chosen value.

Figure 3:
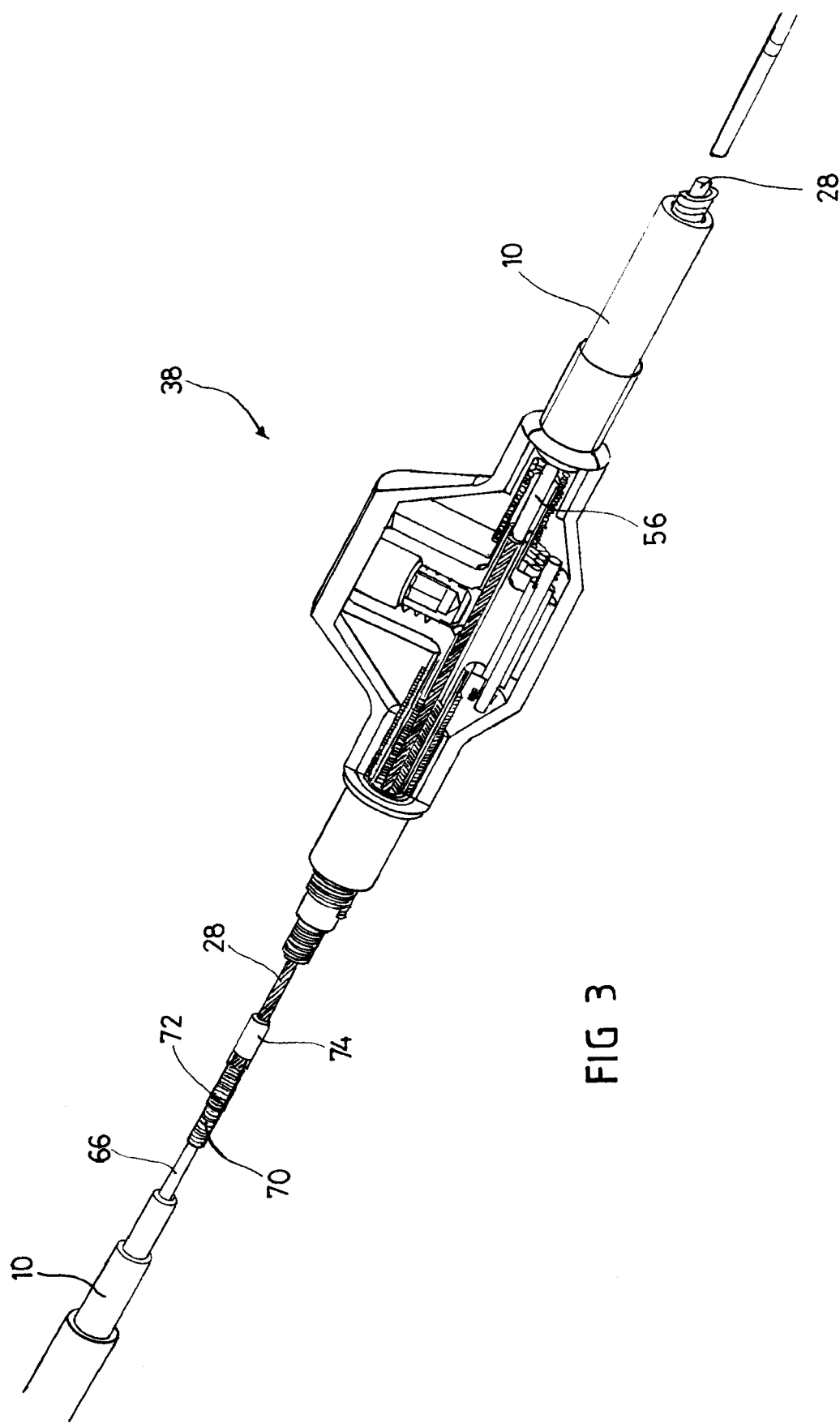
FIG. 3 shows an enlarged and partial cross sectional view of the proximal part region labeled FIG. 3, located in front of connector of the system of FIG. 1.

For this, the present invention proposes to interpose on the lead body 10 an insert 38, integral with the lead body. Insert 38, shown in detail in particular in FIGS. 3 and 4, is located in a proximal region of the lead body, in the vicinity of the connector 20, for example, at about 10 cm from the distal end (that is to say the terminal end of the plug 26) of the connector, in the configuration shown.

Insert 38 includes, as can be seen in particular in the cut-away view of FIG. 4, an interior space defining an interval of interruption 40 of the coiled conductor 18. Conductor 18, in a conventional lead, directly connects the electrode at the distal end of the lead to the connector on the proximal side of this same lead.

On one first (proximal) side of the interval 40, there is a first electrical connection 42 having a coiled conductor connected to a corresponding terminal of the connector 22, namely the ring annular plug 24; on the same side, there is also a second connection 44, for example, a spiral-shaped connector, at the other terminal of the connector 22, i.e., the terminal end tip 26. The two connections 42 and 44 are coaxial connections.

On the other (distal) side of interval 40, there is a third electrical connection, namely a spiral insulated conductor 18 electrically connected to the electrode carried by the distal end of the lead body (the electrode made by the metal tip 16 with the screw 14 in the example shown in FIG. 2).

Insert 38 also includes a body 46 made of a conductive material which is electrically connected to the second electrical connection 44. Body 46 includes a radial threaded hole 48 receiving a screw 50 extending perpendicularly to lead body 10 and thus to microcable 28.

Screw 50 has a flattened end on the interior side 52 for coming into mechanical and electrical contact with a not insulated area 52 of microcable 28 introduced into lead body 10 and insert 38. On the opposite side, the screw 50 has a receptacle or footprint allowing it to be turned by a conventional torque limiting screwdriver tool. Outside region 54, microcable 38 is preferably isolated by coating 56.

Insert 38 also includes a connection 58, axially shifted relatively to the main axis of the insert and of the lead body (i.e., of the microcable). Connection 58 bypasses interval 40 and is attached at a distal side 60 to isolated spiral conductor 18, which is preferably locally bared, and at the proximal side to second electrical connection 42.

In addition, the various elements of insert 38 are enclosed in a sealed housing 64, manufactured, by example, in a molded silicone with lead body 10, which includes a slot for inserting the torque limiting screwdriver.

For its handling, microcable 28 is preferably connected to a pushing stylet 66 (FIGS. 1 and 3), which is a short stylet having at its proximal end an operating handle 68 and at its distal end a spiral tip 70. As shown in FIG. 3, this pushing stylet 66 can be coupled to the proximal end of microcable 28 with a spring-cone 72 formed at the end of microcable 28, and in which the spiral end 70 of stylet 66 can be screwed, in order to establish a temporary connection between the microcable and the pushing stylet. Alternatively, the stylet is terminated at its distal end by a socket created by local deformation of a hypotube, this socket being then directly inserted, with a controlled force on the microcable.

Preferably, an atraumatic tip is formed by the screwing spiral 70 at the end of the pushing stylet 66, which serves to protect the inner lumen of the lead body from a risk of perforation. In addition, the proximal portion of the pushing stylet body may be slightly curved to produce a slight immobilizing friction with the inner lumen of the lead body, to prevent the microcable falling outside of the sterile field of the surgical intervention.

The lead-microcable-pushing stylet system is sized so that when the distal end of the microcable is flush with the end of the lead body and comes into contact with the septum, the pushing stylet is already inserted into the connector for a length of 10 mm, for example. This configuration allows an efficient push for achieving a mechanical puncture of the septum through the rigid pushing stylet, the (soft) microcable being then completely wrapped by the lead body, thus transmitting the compression force while being protected from the risks of folding (wrinkling) that may affect durability.

Moreover, spring-cone 72 of microcable 28 is preferably extended by a ring 74, for example, made of platinum, set with microcable 28, whose diameter is greater than the axial bore of the insert 38. This configuration ensures that microcable 28 will not emerge into the left ventricle beyond a maximum length, and also allows X-ray identification of its proximal end.

Insulation 56 on microcable 28 starts at about 10 cm from its proximal end (screwing cone 72), to ensure an electrical connection after screwing regardless of the emerging length (the emerging length is in it itself limited by the abutment of ring 74). In other words, whatever the emerging length, the part of microcable 28 which is in vis-à-vis the support surface 52 of screw 50 is always a bared portion 54, thus ensuring an electrical contact between microcable 28 and screw 50 and, consequently, with second connection 44.

The configuration as described above thus provides a mechanical and electrical connection for applying, if necessary, RF energy to puncture the septum, and also to test the electrical performance at the time of implantation of the lead (i.e., a mapping of the stimulation site), while allowing an adjustment of the emerging length of microcable 28 in a range from a few millimeters (e.g., for a configuration for pacing the interventricular septum from the side of the left ventricle) to about 120 mm (e.g., for stimulation of the left ventricular free wall).

Another aspect of the present invention is directed to a method for implantation of a system in accordance with a preferred embodiment of the present invention. In one embodiment of the method, the first phase is a classical phase of implantation of the lead, which is to first identify an anchoring site by manipulating distal end 12 of lead 10 through a conventional stylet inserted into the central lumen of the lead. The system is introduced into the superior vena cava, the right atrium and then the ventricle until it butts against the wall of the interventricular septum.

Once the site is reached, the practitioner transmits an axial rotation to the lead body, which has the effect of making the helical screw 14 penetrate the wall of the septum, the complete screw being tactilely detected by the practitioner because of the opposite resistance to the rotation. The axial rotation is applied, as applicable, (i) either directly to the lead body 10 (sheath and spiral conductor 18), (ii) or to the connector plug, for a pin driven lead in the case wherein the proximal connector plug is secured to an axial conductor extending within the lead body, the conductor being itself free to rotate and connected to the helical screw at its distal end.

The site is then confirmed by radiographic examination at different inclinations; if the position is not satisfactory the practitioner can unscrew the lead and move it under control to another point, and then test the new site.

The stylet is then removed and replaced by the microcable which is introduced into the central lumen of the lead until it comes into contact with the septum.

After the microcable has been guided in contact with the wall of the septum, the microcable is connected at its proximal side to a RF puncture generator. The RF energy produced by the generator is applied to the distal end of the microcable, and that energy enables the realization of a very fine puncture in the interventricular septum. The diameter of the puncture is defined by the diameter of the microcable, on the order of 0.3 to 0.5 mm as mentioned above.

After the wall of the septum has been completely traversed, the RF puncture generator is stopped and disconnected from the microcable.

The next step is to push the microcable beyond the septum, now crossed from one side to the other side, so as to let the free portion 30 emerge into the interior volume of the left ventricle beyond the intermediate portion enclosed in the septum. The length of microcable allowed to emerge is a controlled length, typically selected to be between a few millimeters to a few inches, depending on the chosen stimulation configuration (e.g., stimulation of the left ventricle by its free wall, or by its septal wall).

Once the microcable is positioned at the desired location, the surgeon tightens screw 50 of insert 38. The microcable 28 is then locked and secured in rotation (and also in translation) from the lead body 10, allowing an easy manual unscrewing of the pushing stylet 66. The compressive force exerted by screw 50 and therefore the stress exerted on the microcable, is controlled by the limiting torque of the torque screwdriver used.

From a mechanical point of view, it must be noted that there are several functions of the lead:
  Selection of the puncture site of the septum;
  Guiding of the microcable during the intravenous route;
  Transmission of the push to the end of the microcable during the puncture;
  Microcable stabilization during the septal RF puncture;
  Definition (orientation) of the path of the microcable during the RF puncture, with the possibility to test several implantation configurations;
  Finally, stabilization and protection of the long length of the microcable on the venous side throughout the lifetime of the device.

It must also be noted that the system is perfectly reversible, both during the implantation intervention and post-operative.

From an electrical point of view, once screw 50 of insert 38 is tightened a two lines configuration is met with:
  A stimulation line including, successively: microcable 28 (whose active part emerges into the left ventricle), screw 50, second connection 44 and terminal end tip 26 of connector 22, and
  A bipolar line comprising, successively: a bipolar electrode carried by the lead head and formed by tip 16 with screw 14 (in contact with the wall of the right ventricle), isolated spiral conductor 18, connection 58 bypassing the interval 40, first connection 42 and ring annular terminal 24 of the terminal connector 22.

The isolation of the two lines in insert 38 is obtained in a conventional manner by, e.g., a silicone adhesive.

The system just described may alternatively be implemented on a lead extension instead of directly on the lead itself. In this case, insert 38 is arranged on a bipolar IS-1/bipolar IS-1 extension that is connected to a conventional lead, allowing the use of a microcable with an already implanted left ventricular lead.

With regard to an embodiment having an application to a pacing lead implanted in the coronary system, such as described in French patent application No. 10/59521 and its counterpart U.S. Ser. No. 13/300,451, cited above, the anchoring screw at the distal end of the lead is replaced by a retaining means in the vein at this end. This retaining means is, for example, made of a silicone screw of the same type as that used by the Situs LV lead marketed by Sorin CRM (Clamart, France) and described in EP 0993840 A1 (ELA Medical). On the other hand, this terminal does not include an electrode and the various corresponding elements described above may be omitted.

Finally, whether the stimulation is delivered endocardially or from a vein in the coronary system, the invention applies, mutatis mutandis, to a lead provided with a plurality of microcables arranged in a corresponding plurality of internal lumens of the lead body, providing for the various microcables a corresponding number of electrical connections and the respective inserts.

One skilled in the art will appreciate that the present invention may be practiced by other than the embodiments described herein, which are provided for purposes of illustration and not of limitation.

The invention claimed is:

1. A system for stimulation/defibrillation of a left ventricle endocardially or from a vein in a coronary system, comprising:
  a lead body made of a deformable material and having an inner lumen, at least one insulated conductor extending along an entire length of the lead body and at least one stimulation/defibrillation electrode;

a first distal end of the lead body having an anchor for anchoring to a wall of a heart chamber or to a vein of the coronary system, and a proximal end of the lead body having a connector including a first terminal and a second terminal connected to the stimulation/defibrillation electrode via said insulated conductor extending along the lead body, and a single microcable—that is electrically conductive, and housed in and slidable along the inner lumen of the lead body extending the entire length of the lead body and beyond the first distal end of the lead body, said microcable having a second distal end including an active free part comprising a bare area, and an insert formed on the lead body in a proximal region thereof, said insert comprising:
- a proximal side having a first electrical connection to said first terminal connector and a second electrical connection to said second terminal of the connector;
- a distal side having a third electrical connection to the insulated conductor;
- a coupler, having (i) a released position wherein the microcable is free to slide in the inner lumen of the lead body and (ii) a closed position, wherein the microcable is both mechanically immobilized in the lead body and electrically connected to said first electrical connection via the coupler, and is actuatable between the released and closed positions;

wherein said insert is electrically isolated and includes an interruption of the insulated conductor; and a connection, bypassing the interruption, from the second electrical connection to the third electrical connection.

2. The system of claim 1, wherein the coupler further comprises a screw radially oriented relative to the length of the lead body, with an inner end penetrating into the interruption to come in radial support against the microcable and an outer end including a receptacle for receiving a screwing tool.

3. The system of claim 1 further comprising a stylet for pushing the microcable in the lead body and having a stylet distal end, and
wherein the microcable is terminated at its proximal end by a receptacle for receiving the stylet distal end.

4. The system of claim 3, wherein the receptacle is a hollow spring-cone shape, screwed with the distal end of the pushing stylet.

5. The system of claim 1 further comprises a stylet for pushing the microcable in the lead body and wherein the microcable is terminated at its proximal end by a socket created by local deformation of a hypotube and wherein the stylet is directly inserted with a controlled force into the microcable.

6. The system of claim 1 further comprising a stylet for pushing the microcable in the lead body, and wherein the stylet is terminated at its distal end by a socket created by local deformation of a hypotube.

7. The system of claim 1, wherein the lead body and the microcable are dimensioned so that when the distal end of the microcable passes through the inner lumen of the lead body, the microcable is then completely introduced into-an assembly formed by the lead body and the connector.

8. The system of claim 1, wherein the microcable further comprises a stop ring near its proximal end in a region between the proximal end of the microcable and the insert formed on the lead body, the diameter of the stop ring being greater than—a diameter of—a bore of the insert formed on the lead body and receiving the microcable at proximal end, so as to limit the sliding of the microcable in the lead body, and a length of an emerging distal part of the microcable beyond a predetermined maximum length.

9. The system of claim 1, wherein the lead comprises at least a first portion and an extension portion separable from each other, wherein (i) the first portion comprises the lead and a proximal first plug terminating at said proximal end, and (ii) the extension portion comprises a second plug terminating at said distal end, wherein the insert is formed on the extension portion.

\* \* \* \* \*